(12) United States Patent
Bugamelli et al.

(10) Patent No.: US 11,298,493 B2
(45) Date of Patent: Apr. 12, 2022

(54) STABILIZED MASK

(71) Applicant: KONINKLIJKE PHILIPS N.V., Eindhoven (NL)

(72) Inventors: Antonio Bugamelli, Mars, PA (US); Lauren Patricia Chodkowski, Pittsburgh, PA (US); Duon Alex Truong, Plum Borough, PA (US)

(73) Assignee: Koninklljke Philips N.V., Eindhoven (NL)

( * ) Notice: Subject to any disclaimer, the term of this patent is extended or adjusted under 35 U.S.C. 154(b) by 1122 days.

(21) Appl. No.: 14/889,469

(22) PCT Filed: Apr. 29, 2014

(86) PCT No.: PCT/IB2014/061069
§ 371 (c)(1),
(2) Date: Nov. 6, 2015

(87) PCT Pub. No.: WO2014/181214
PCT Pub. Date: Nov. 13, 2014

(65) Prior Publication Data
US 2016/0082215 A1    Mar. 24, 2016

Related U.S. Application Data

(60) Provisional application No. 61/821,370, filed on May 9, 2013.

(51) Int. Cl.
*A61M 16/06*    (2006.01)

(52) U.S. Cl.
CPC ........ *A61M 16/0622* (2014.02); *A61M 16/06* (2013.01); *A61M 16/0666* (2013.01); *A61M 16/0683* (2013.01); *A61M 2210/0618* (2013.01)

(58) Field of Classification Search
CPC .............. A61M 16/06; A61M 16/0622; A61M 16/0666; A61M 16/0683; A61M 16/0618; A61M 2210/0618
See application file for complete search history.

(56) References Cited

U.S. PATENT DOCUMENTS

| 6,520,182 B1 | 2/2003 | Genaratnam |
| 9,095,673 B2 | 8/2015 | Barlow |

(Continued)

FOREIGN PATENT DOCUMENTS

| CN | 101389368 A | 3/2009 |
| CN | 103052421 A | 4/2013 |

(Continued)

OTHER PUBLICATIONS

Disclosed Anonymously, "Improvements Relating to Respiratory Interface Devices", ip.com 000172009D, Jun. 25, 2008.

*Primary Examiner* — Colin W Stuart
*Assistant Examiner* — Douglas Y Sul
(74) *Attorney, Agent, or Firm* — Michael W. Haas

(57) ABSTRACT

A patient interface device includes a cushion defining a cavity therein, the cushion having a first side and an opposite second side. An aperture is formed in the second side and provides access to the cavity, the aperture having a periphery adapted to sealingly engage about the nostrils of a patient when the cushion is disposed on the face of a patient. The patient interface device further includes a pair of stabilizing members coupled to, and extending from, the cushion, each stabilizing member being adapted to contact the face of the patient in the adjacent nasal region below the orbital bone ridge in such a manner that strapping forces, which would otherwise be directed near the nares of the patient, are instead concentrated onto the patient's maxilla.

20 Claims, 9 Drawing Sheets

(56) References Cited

U.S. PATENT DOCUMENTS

| | | |
|---|---|---|
| 2005/0199241 A1 | 9/2005 | Ging |
| 2005/0199242 A1* | 9/2005 | Matula, Jr. ............ A61M 16/06 128/207.13 |
| 2006/0060200 A1 | 3/2006 | Ho |
| 2006/0201514 A1* | 9/2006 | Jones ................ A61M 16/0683 128/206.21 |
| 2007/0163594 A1 | 7/2007 | Ho |
| 2007/0163600 A1 | 7/2007 | Hoffman |
| 2008/0289633 A1 | 11/2008 | Kwok |
| 2009/0032024 A1* | 2/2009 | Burz .................... A61M 16/06 128/206.24 |
| 2009/0120442 A1 | 5/2009 | Ho |
| 2011/0000492 A1* | 1/2011 | Veliss ............... A61M 16/0666 128/207.13 |
| 2011/0146685 A1* | 6/2011 | Allan .................... A61M 16/06 128/205.25 |
| 2011/0155139 A1 | 6/2011 | Ho |
| 2011/0155140 A1* | 6/2011 | Ho .................... A61M 16/0666 128/207.18 |
| 2012/0067349 A1* | 3/2012 | Barlow ................ A61M 16/06 128/205.25 |
| 2013/0014760 A1 | 1/2013 | Matula, Jr. |
| 2013/0037030 A1* | 2/2013 | Matula, Jr. ........ A61M 16/0816 128/205.25 |
| 2014/0090649 A1* | 4/2014 | Groll .................... A61M 16/06 128/205.25 |
| 2015/0209541 A1* | 7/2015 | Harwood .......... A61M 16/0666 128/205.25 |

FOREIGN PATENT DOCUMENTS

| | | |
|---|---|---|
| JP | 2012528608 A | 11/2012 |
| WO | WO2004078228 A2 | 9/2004 |
| WO | WO2005118040 A1 | 12/2005 |
| WO | WO2012020359 A1 | 2/2012 |
| WO | WO2012085758 A1 | 6/2012 |

\* cited by examiner

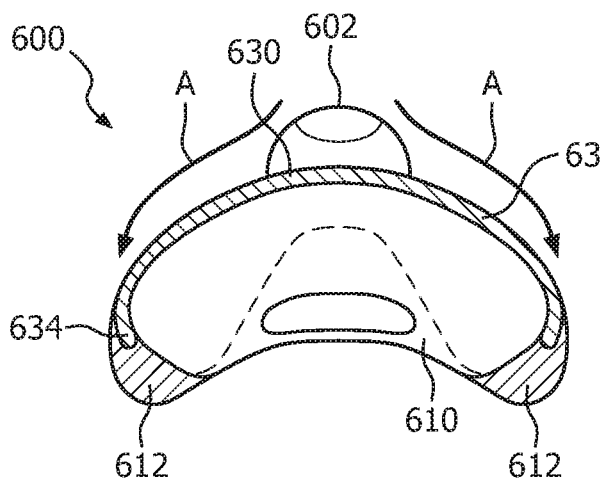
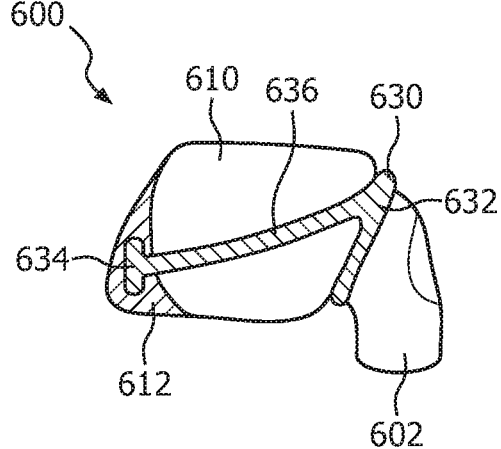
FIG. 15A  FIG. 15B
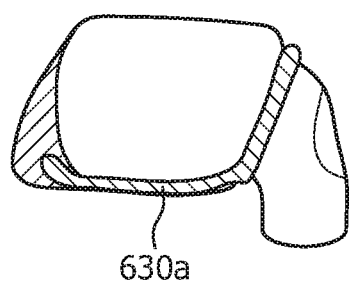
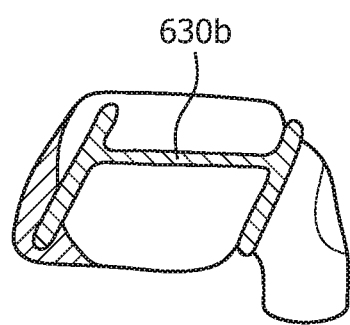
FIG. 16A  FIG. 16B

STABILIZED MASK

CROSS-REFERENCE TO RELATED APPLICATIONS

This patent application claims the priority benefit under 35 U.S.C. § 371 of international patent application no. PCT/IB2014/061069, filed Apr. 29, 2014, which claims the priority benefit under 35 U.S.C. § 119(e) of U.S. Provisional Application No. 61/821,370 filed on Mar. 9, 2013, the contents of which are herein incorporated by reference.

BACKGROUND OF THE INVENTION

1. Field of the Invention

The present invention generally relates to nasal masks, and, more particularly, to nasal masks having stabilizing elements.

2. Description of the Related Art

There are numerous situations where it is necessary or desirable to deliver a flow of breathing gas non-invasively to the airway of a patient, i.e., without intubating the patient or surgically inserting a tracheal tube in the esophagus. For example, it is known to ventilate a patient using a technique known as non-invasive ventilation. It is also known to deliver continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear assembly having one or more straps adapted to fit over/around the patient's head.

Patients that require pressure support therapy are often confronted with the problem of finding a suitable patient interface device. In finding a suitable patient interface device, such patients frequently struggle with issues relating to the seal and stability of the patient interface device, the comfort of the patient interface device, the size/weight of the patient interface device and the sizing of the patient interface device. These challenges, if not addressed properly, can compromise the patient's compliance with the prescribed therapy.

Nasal masks often appeal to patients as such masks offer attractive advantages to patients due to the fact that they tend to be lighter, provide reduced facial contact, and tend to not restrict the patient's field of vision. Conventional nasal masks typically are one of two primary configurations. Pillows masks are the most commonly adopted configuration and are typically comprised of two channels projecting directly into the separate nasal cavities of the patient. Mounted atop these two channels are soft, compliant, pillows that seal generally in and around the patient's individual nostrils. Additionally, these two channels are conjoined in a central manifold which receives that piped pressure from a pressure delivery system to which the mask is coupled. The arrangement of such pillows generally serves to anchor such masks to a patient's face.

The second common configuration utilizes a cradle cushion. Attached directly to the central manifold, a cut-out is applied which allows both nostrils to receive pressure while simultaneously sealing on the periphery of the nostril openings and upper lip. This configuration has generally not been received in the market place as well as the pillows mask. Without having pillows to anchor the mask, the mask commonly becomes very unstable. One way to resolve this problem is to add support to the headgear to hold the cushion firmly in place, unfortunately there is a negative connotation with hard or bulky material that is used to create this support. Continued focus on reducing the form factor of the cradle cushion has resulted in further reduction in stability of the mask. As stability reduces, air leakage occurs and patients are forced to apply more strapping force, which significantly reduces the comfort of the mask and compliance for patients.

SUMMARY OF THE INVENTION

Accordingly, it is an object of the present invention to provide a patient interface device that overcomes the shortcomings of conventional designs. The patient interface device comprises: a cushion defining a cavity therein, the cushion having a first side and an opposite second side; an aperture formed in the second side providing access to the cavity, the aperture having a periphery adapted to sealingly engage about the nostrils of a patient when the cushion is disposed on the face of the patient; and a pair of stabilizing members coupled to, and extending from, the cushion, each stabilizing member being adapted to contact the face of the patient in the adjacent nasal region below the orbital bone ridge in such a manner that strapping forces, which would otherwise be directed near the nares of the patient, are instead concentrated onto the patient's maxilla.

The stabilizing members may be disposed on opposite sides of the aperture. Each of the stabilizing members may be integrally formed with the cushion. Each of the stabilizing members may be bounded by a grooved portion which is structured to allow each stabilizing member to articulate with respect to the cushion. The grooved portion may comprise a baffle. The grooved portion may comprise a locally thinned wall section. The stabilizing members may be formed separately from, and selectively coupled to, the cushion. Each stabilizing member may comprise a cavity formed therein. Each cavity may be in communication with the cavity of the cushion and each cavity may be adapted to be inflated by one or both of the applied system pressure and the exhalation pressure of the patient. Each cavity may be filled with one or more of a low durometer gel or foam. The cushion may comprise a generally cradle shaped elongate hollow body and the first side may be is of a generally convex shape and the opposite second side may be of a generally concave shape. The patient interface device may further comprise a generally rigid elongated front portion coupled to the front side of the cushion, the front portion having a first end, an opposite second end and an aperture disposed therebetween, wherein the aperture is adapted to be coupled to a patient circuit and wherein each of the first end and opposite second end may be adapted to be selectively coupled to a headgear for use in securing the patient interface device to the head of a patient. The front portion may be coupled to the front side of the cushion via a hollow articulating portion. The hollow articulating portion may include an inward curved U-shaped portion disposed along an upper portion thereof.

BRIEF DESCRIPTION OF THE DRAWINGS

FIG. 15A is a top cross-sectional view and FIG. 15B is a side view of a further embodiment of a patient interface device including a maxilla support assembly according to the principles of the present invention; and FIGS. 16A-16B are side views of patient interface devices showing alternative embodiments for the maxilla support assembly of FIG. 15A and 15B.

DETAILED DESCRIPTION OF EXEMPLARY EMBODIMENTS

Figure 1:
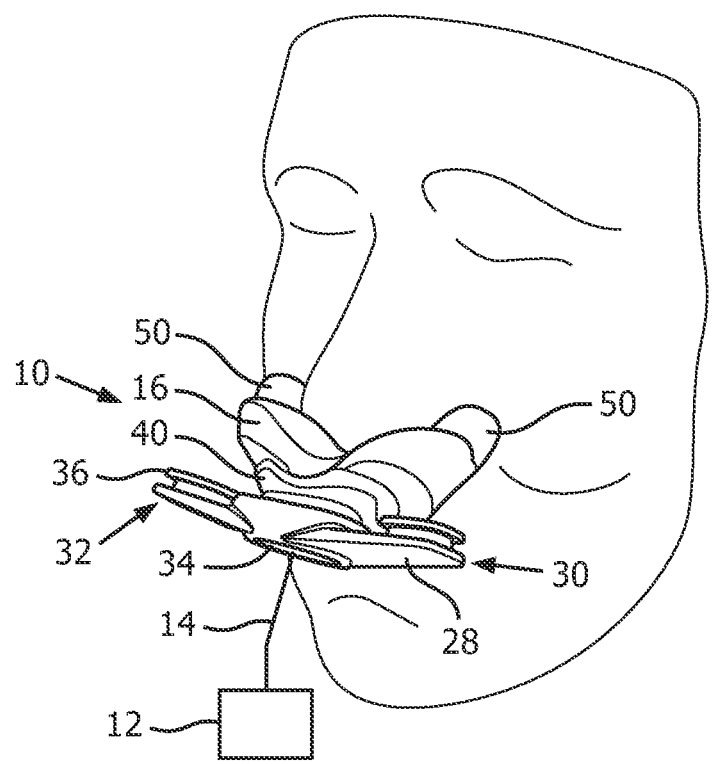
FIG. 1 is a front isometric view of an example embodiment of a patient interface device according to the principles of the present invention disposed on the face of a patient and shown schematically connected to a pressure support system.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, "selectively coupled" shall mean that the parts are joined or operate together in a manner such that the components may be separated or uncoupled and then recoupled as desired.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality). As employed herein, the term "and/or" shall mean both alternatives (i.e., "and") or just one of the alternatives (i.e., "or").

Directional phrases used herein, such as, for example and without limitation, top, bottom, left, right, upper, lower, front, back, and derivatives thereof, relate to the orientation of the elements shown in the drawings and are not limiting upon the claims unless expressly recited therein. Like numbers refer to like elements throughout.

Embodiments of the present invention provide improved stability to masks used in delivering a flow of a treatments gas to the airway of a patient. Particular exemplary embodiments address constraints in reducing the size of a cradle mask by providing a number of structures which enhance stability and reduce movement of the mask with respect to the face of a patient.

FIGS. 1-8 illustrate an exemplary embodiment of a patient interface device 10 according to the principles of the present invention. Referring to FIG. 1, patient interface device 10 is shown disposed on the face (not numbered) of a patient and schematically connected to a pressure support system 12 via a patient circuit 14, which communicates gas from pressure support system 12 to patient interface device 10. Patient circuit 14 is any device, such as flexible tubing, that carries the flow of gas from the pressure/flow generator in pressure support system 12 to patient interface device 10. Pressure support system 12 is any conventional ventilation or pressure support system. Examples of such pressure support systems include, but are not limited to, a ventilator, a continuous positive airway pressure (CPAP) device, or a variable pressure device, e.g. an auto-titrating device, proportional assist ventilation (PAV®) device, proportional positive airway pressure (PPAP®) device, C-Flex™ device, Bi-Flex™ device, or a BiPAP® device manufactured and distributed by Philips Respironics of Murrysville, Pa., in which the pressure provided to the patient varies with the patient's respiratory cycle so that a higher pressure is delivered during inspiration than during expiration, or other pressure support device.

Figure 2:
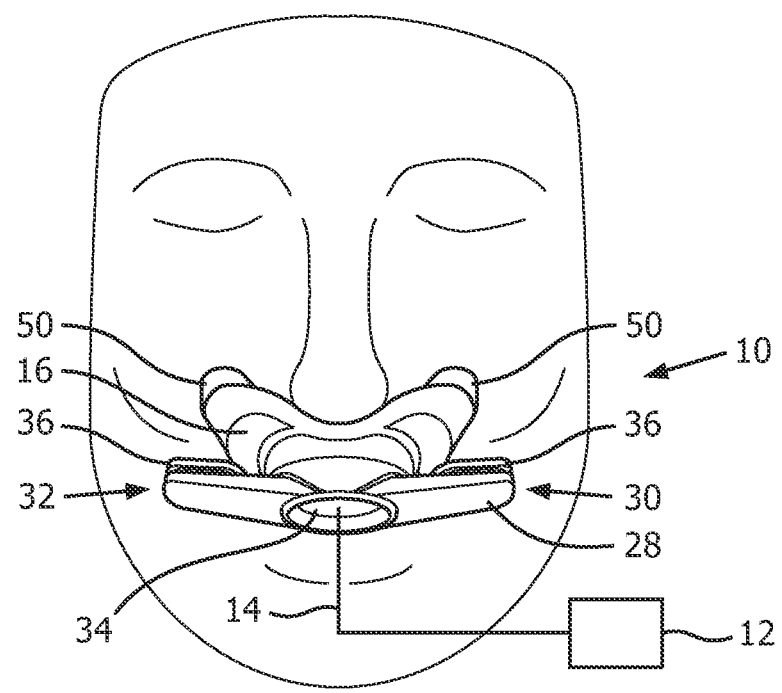
FIG. 2 is a front elevation view of the arrangement of FIG. 1.
Figure 3:
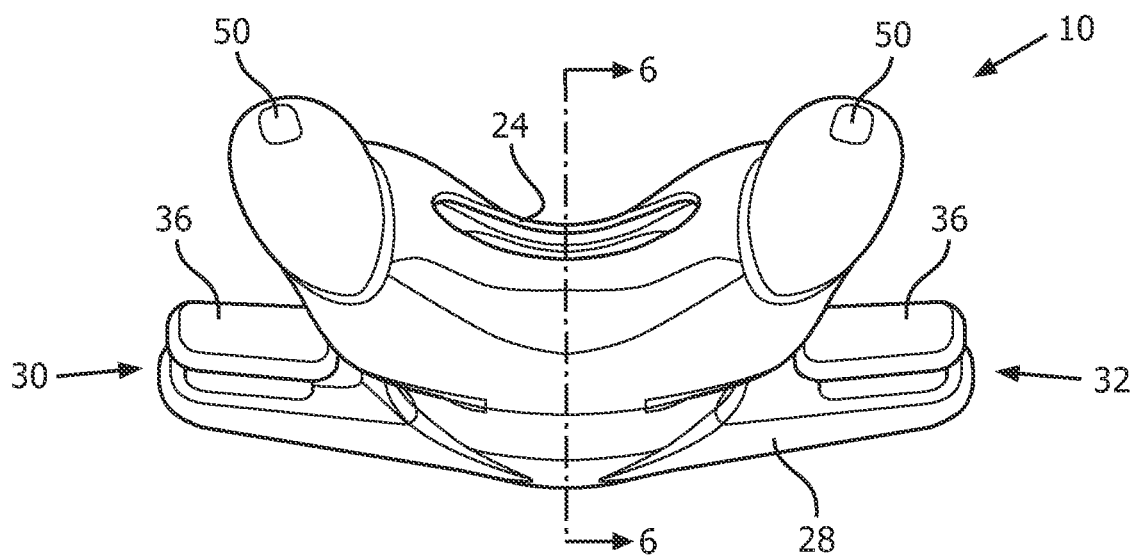
FIG. 3 is a rear elevation view of the patient interface device of FIG. 1.
Figure 4:
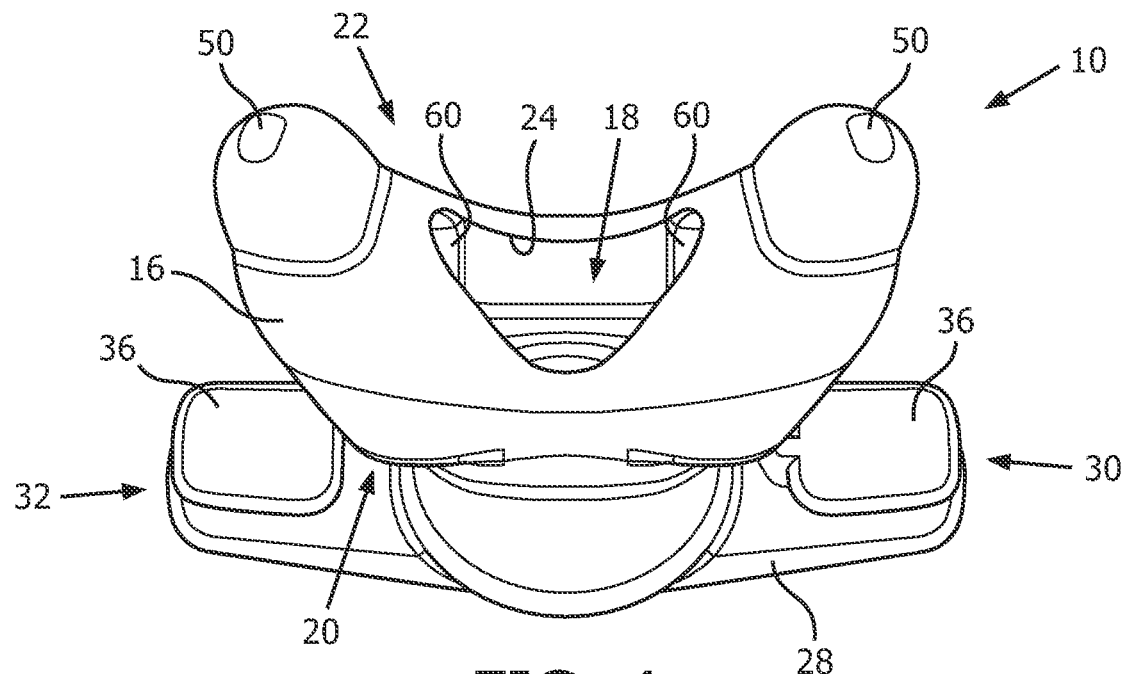
FIG. 4 is a top view of the patient interface device of FIG. 1.

Patient interface device 10 includes a cushion 16 sized and configured to span at least a portion of a patient's face while remaining below the patient's eyes when patient interface device 10 is disposed on the face of a patient, such as shown in FIGS. 1 and 2. Cushion 16 comprises a generally cradle shaped elongate hollow body defining a cavity 18 therein and includes a generally convex shaped front side 20 and a generally concave shaped rear side 22, as shown in the top view of FIG. 4. An opening 24, disposed in rear side 22, provides access to cavity 18. The periphery (not numbered) of opening 24 is adapted to sealingly engage about the nostrils of a patient when patient interface device 10 is disposed on the face of a patient.

Patient interface device 10 further includes a generally rigid elongated front portion 28 having a first end 30, an opposite second end 32 and an aperture 34 disposed therebetween which is adapted to be coupled (either directly or indirectly) to patient circuit 14 via any suitable coupling mechanism. As perhaps best shown in the front view of FIG. 2, front portion 28 is wider than body portion 16. A coupling mechanism, such as the snap like coupling mechanisms 36 illustrated in the FIGS., is provided at or about each of first and second ends 30 and 32 for selectively coupling patient interface device 10 to a headgear (not shown) used in securing patient interface device 10 to the head of a patient.

It is to be appreciated that a variety of coupling mechanisms, slots, or other suitable coupling arrangements may be employed in conjunction with any of a large variety of headgear assemblies for securing patient interface device 10 to the head of a patient without varying from the scope of the present invention.

Figure 5:
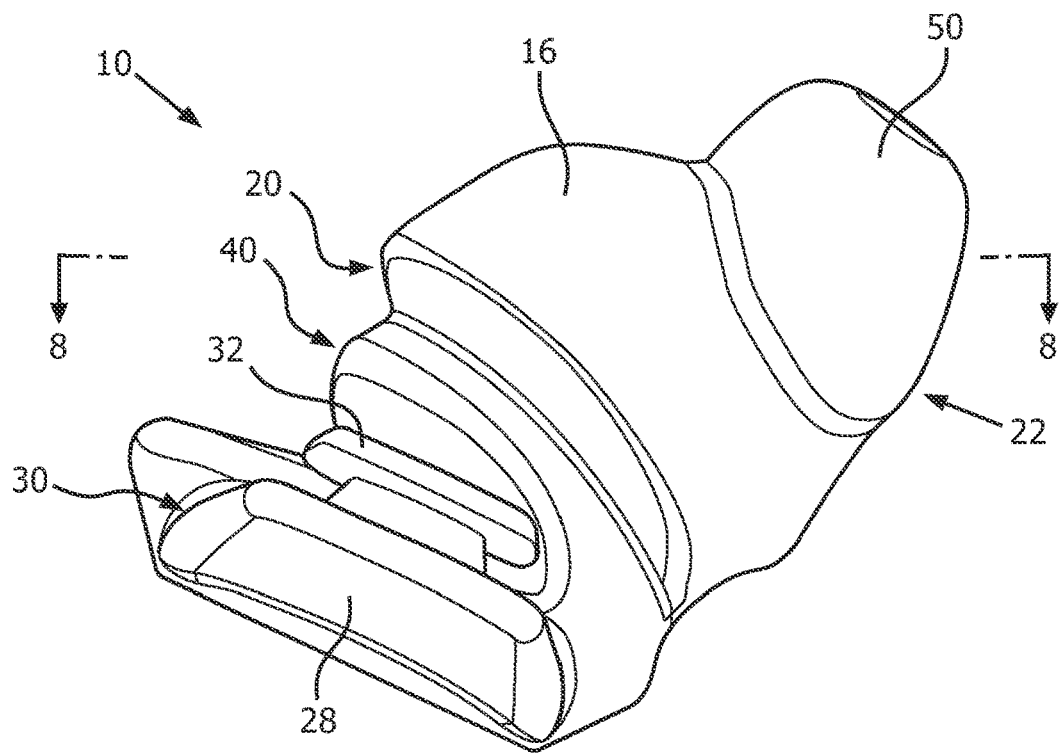
FIG. 5 is a side view of the patient interface device of FIG. 1.
Figure 6:
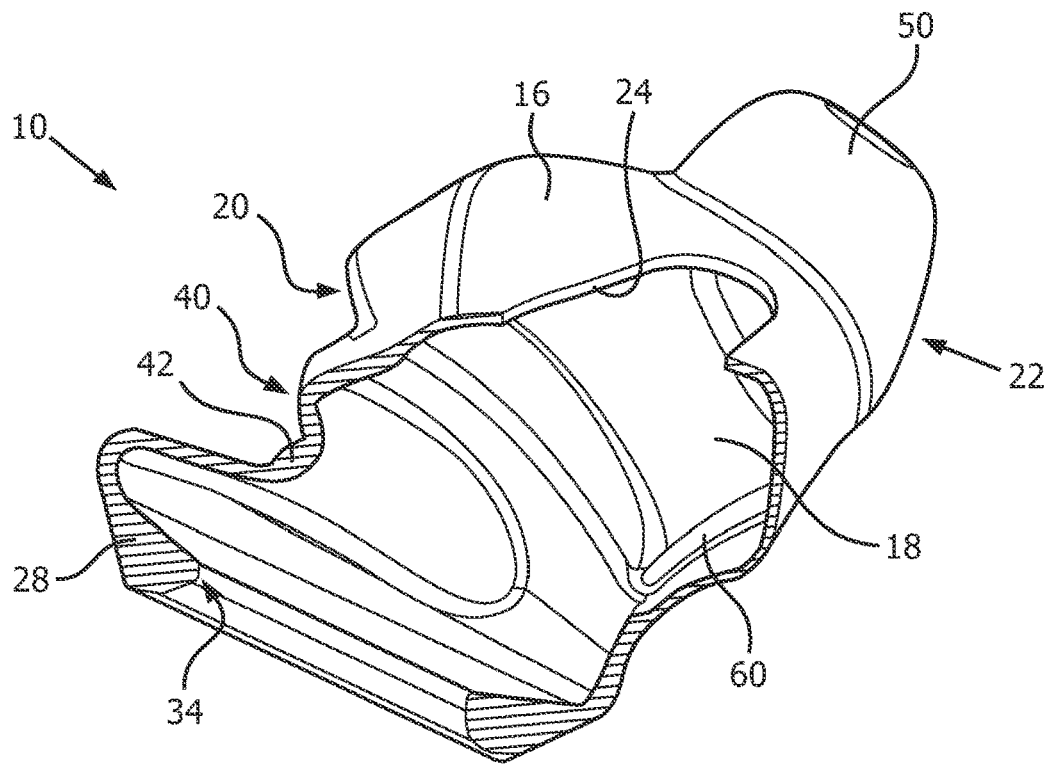
FIG. 6 is a sectional view of the patient interface device of FIG. 1 taken along line 6-6 of FIG. 3.
Figure 7:
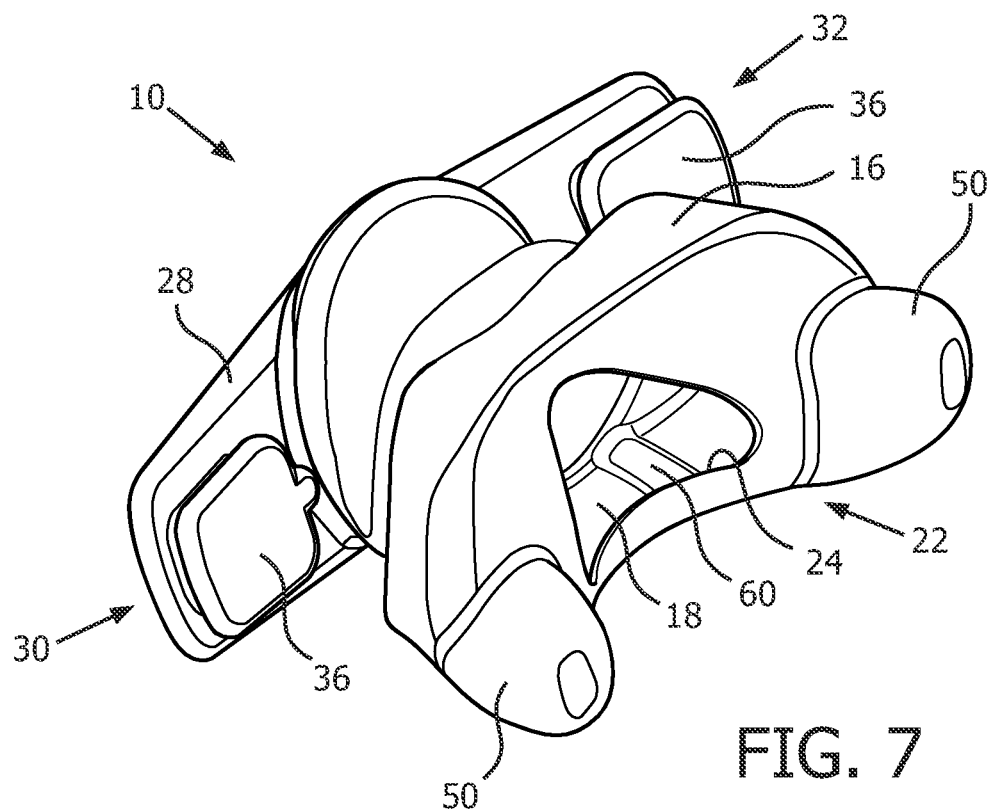
FIG. 7 is an isometric rear view of the patient interface device of FIG. 1.

Referring to the side and sectional side views of FIGS. 5 and 6, front portion 28 is coupled to rear side 22 of cushion 16 via a hollow articulating portion 40 having an inward curved U-shaped portion 42 (FIG. 6) disposed along an upper portion thereof. It is to be appreciated that such arrangement allows for one or both of cushion 16 and front portion 28 to generally be able to move one or more of up, down, and side-to-side with respect to the other of cushion 16 and front portion 28 via flexure of articulating portion 40. As can be readily appreciated from the sectional view of FIG. 6, treatment gas received at aperture 34 from pressure support system 12 via patient circuit 14 (as previously discussed) is communicated to cavity 18 within cushion 16 via hollow articulating portion 40. As shown in the example embodiment illustrated in FIGS. 1-8, patient interface device 10 may be formed from a single integral elastomeric material (e.g., without limitation, silicone). In example embodiments, materials having a durometer in the range of about 30 Shore A to about 60 Shore A have been utilized. It is to be appreciated, that the present invention also contemplates that patient interface device 10 may be formed from multiple components formed from the same or different materials which are then coupled together, either permanently or selectively.

Figure 14A:
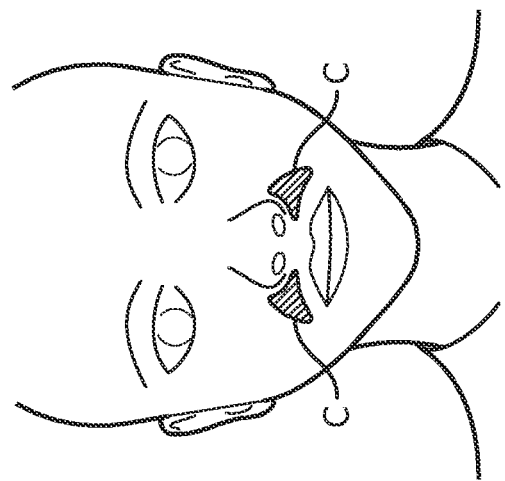
FIGS. 14A-14C are examples of contact areas on a patient's face for stabilizing members in accordance with principles of the present invention.
Figure 14B:
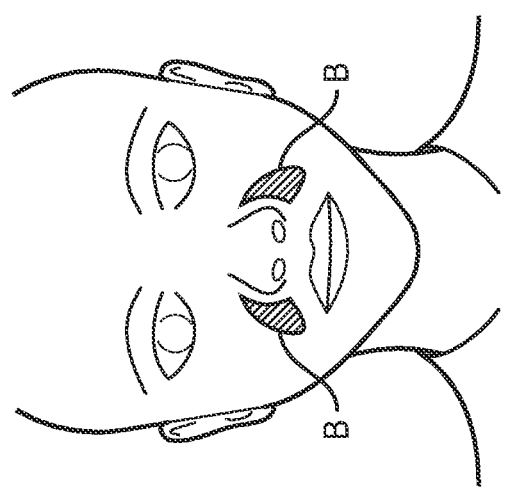
Figure 14C:
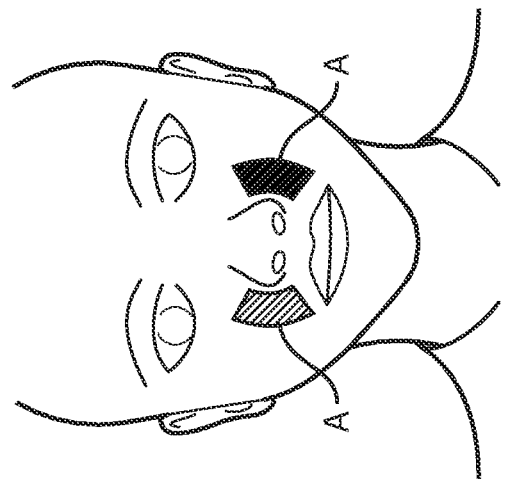

In order to help stabilize patient interface device 10, and more particularly cushion 16 on the face of a patient, cushion 16 further includes a pair of stabilizing members 50 disposed on generally opposite sides of opening 24. As shown in FIGS. 1 and 2, each stabilizing member 50 is adapted to contact the face of a patient in the adjacent nasal region generally below the orbital bone ridge in such a manner that strapping forces, which would otherwise be directed near the nares of the patient, are instead concentrated onto the patient's maxilla. FIGS. 14A-14C, respectively, show non-limiting examples of different regions or areas of contact A, B, C that embodiments of stabilizing members 50 may make on a patient's face. Region A (FIG. 14A) is an example of a support area which generally provides high stability from hose torque/weight in all directions. Regions B and C are examples of support areas of lesser size than region A (and therefore generally reduce the profile of the associated mask) and focus more on supporting against downward hose torque.

Figure 8:
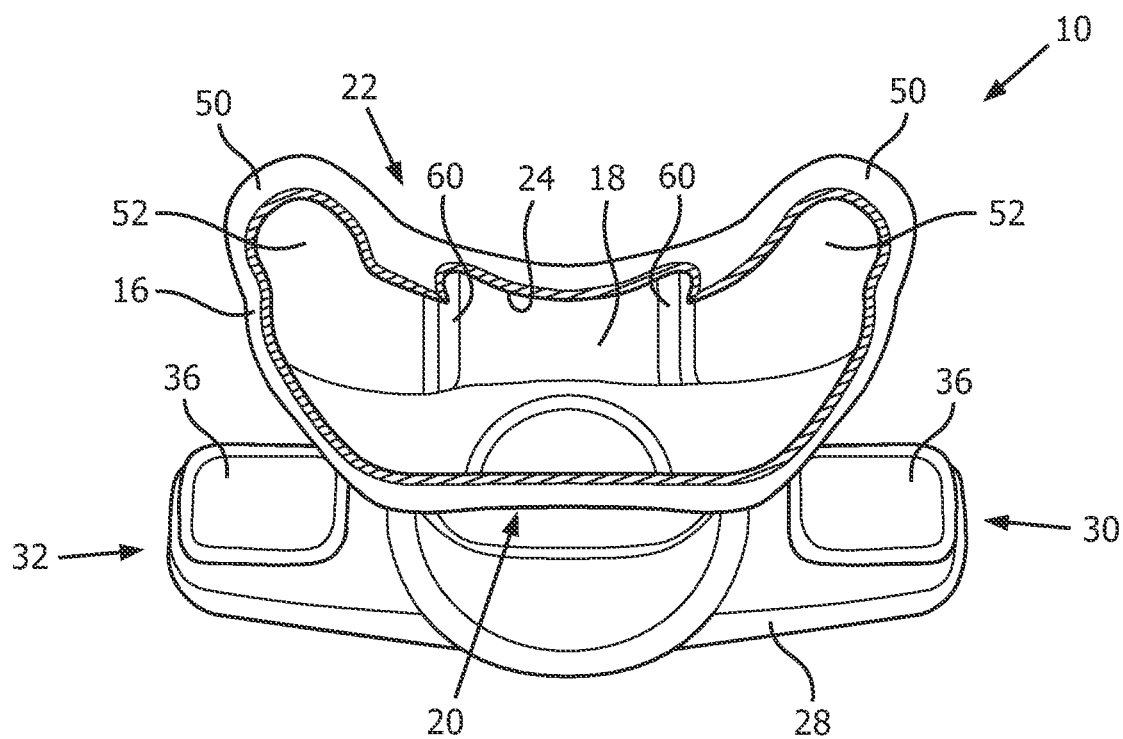
FIG. 8 is a sectional view of the patient interface device of FIG. 1 taken along line 8-8 of FIG. 5.

As shown in the sectional view of FIG. 8, each stabilizing member 50 includes a cavity 52 which, in the embodiment of FIGS. 1-8 is generally inflated by one or both of the applied system pressure and the exhalation pressure of the patient.

Figure 9:
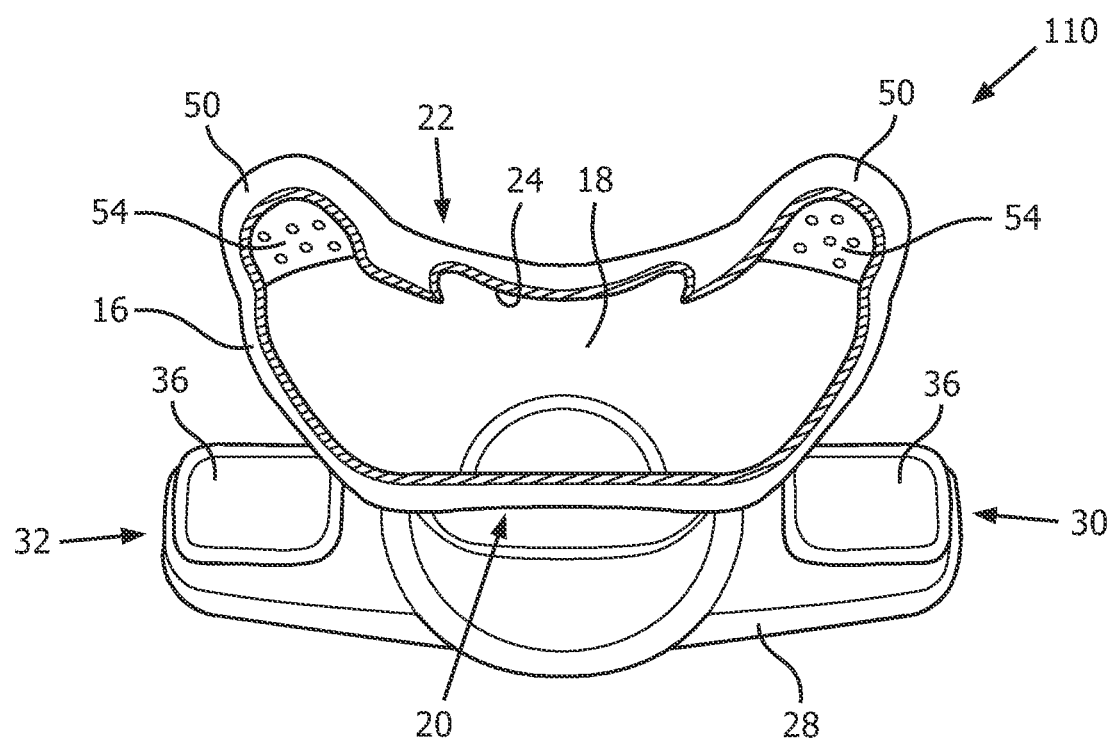
FIG. 9 is a sectional view similar to the sectional view of FIG. 8 of another embodiment of a patient interface device according to the principles of the present invention.

As shown in the example patient interface device 110 of FIG. 9, each stabilizing member 50 may be generally filled with a low durometer gel (e.g.,<10 shore A), foam, or other soft material 54 to modify the stiffness or feel of stabilizing members on the patient's face.

Figure 10:
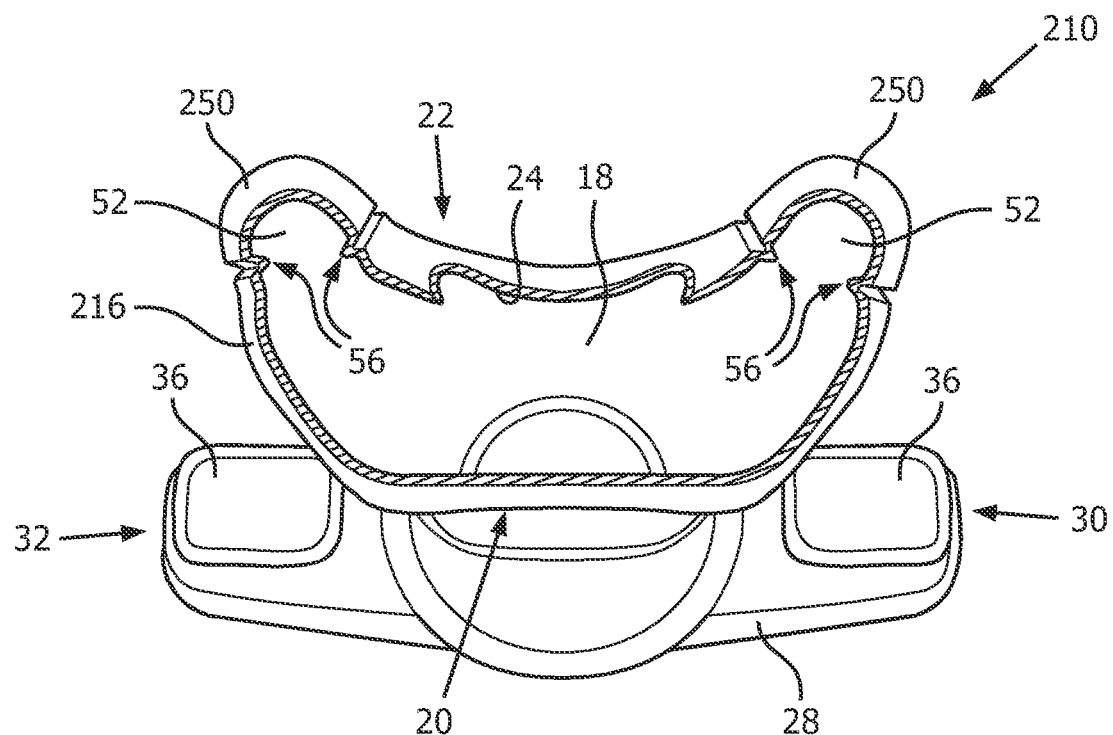
FIGS. 10-13 are sectional views similar to the sectional views of FIGS. 8 and 9 of further embodiments of patient interface devices according to the principles of the present invention.

FIG. 10 shows a sectional view of another example patient interface device 210 having stabilizing members 250 bounded by a grooved portion 56 which generally allows for each of stabilizing members 250 to articulate with respect to cushion 216. Such articulation further improves the stability of patient interface 210 by allowing each of stabilizing members 250 to displace and maintain contact with the maxilla of the patient as the patient moves throughout a sleep cycle. Each of grooved portions 56 may include one or more baffles/rolls or be comprised of a thinned wall section (with respect to the adjacent wall sections) which allow displacement of each stabilizing member 250 while also providing for such members 250 to return to their original position when no force is applied thereto.

Figure 11:
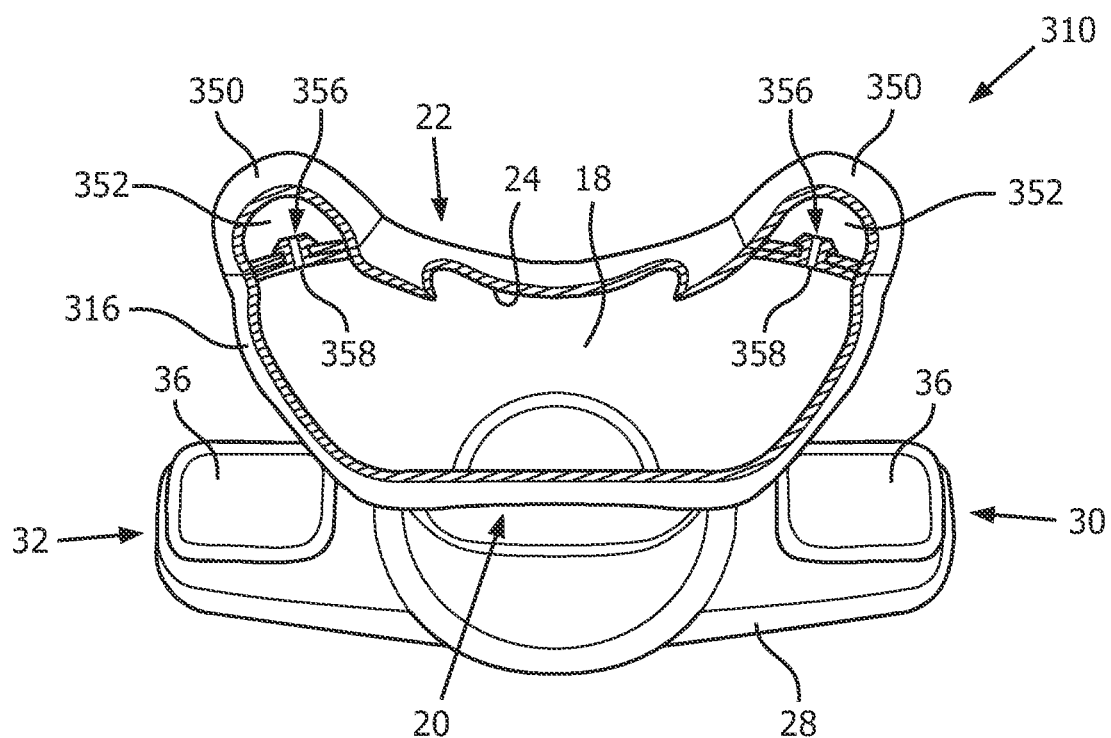

FIG. 11 shows a sectional view of yet another example patient interface device 310 having stabilizing members 350 which are selectively coupled to cushion 316 via the interaction of one or more coupling mechanisms provided on each stabilizing member 350 and cushion 316. In the example embodiment shown in FIG. 11, such coupling mechanisms include a mushroom shaped protrusion 356 which extends from cushion 316 and is engaged by a cooperatively shaped aperture 358 formed in stabilizing member 350. It is to be appreciated, however, that other suitable coupling mechanisms may be employed without varying from the scope of the present invention. It is also to be appreciated that such arrangement allows for the stabilizing members to be selectively replaced, if needed, or custom tailored to fit a particular patient by changing one or more of the size, texture, hardness, etc. of the stabilizing member.

Continuing to refer to FIG. 11, similar to the embodiment shown in FIG. 8, each of stabilizing members 350 includes a hollow cavity 352 in fluid communication with cavity 18 via a channel 360 formed in each mushroom shaped protrusion 356. Such arrangement provides for each cavity 352 to be generally inflated by one or both of the applied system pressure and the exhalation pressure of the patient.

Figure 12:
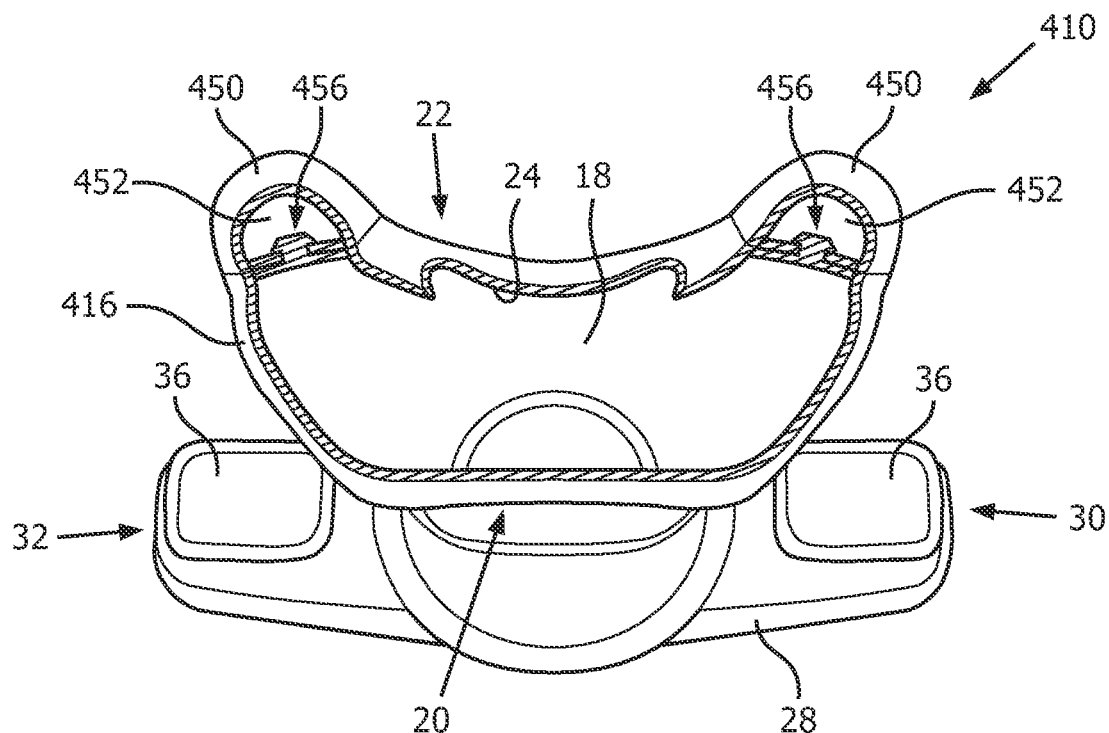
Figure 13:
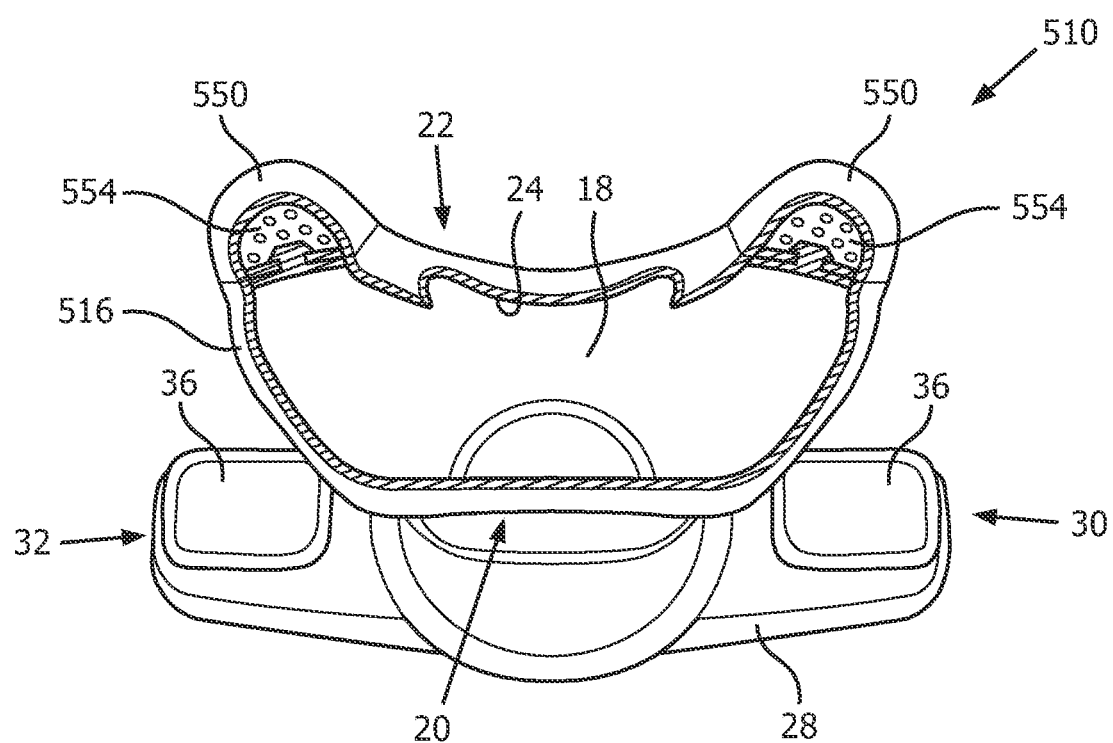

FIG. 12 shows a sectional view of a further example patient interface device 410 similar to that shown in FIG. 11, except each selectively coupled stabilizing member 450 includes a sealed cavity 452 which is not in communication with cavity 18. In such arrangement, cavity 452 may be filled with air of a predetermined pressure in order to provide a selected stiffness for each member 450. As shown in the example patient interface 510 of FIG. 13, each stabilizing member 550 may similarly be generally filled with a low durometer gel, foam, or other soft material 554 to modify the stiffness or feel of the stabilizing members 550 on the patient's face.

Although only one pair of stabilizing members 50, 150, 250, 350 and 450 are included in the example embodiments of FIGS. 8-13, it is to be appreciated that one or more of the quantity, size or shape of such stabilizing members may be modified without varying from the scope of the present invention.

As yet another stabilizing feature, the embodiment of FIGS. 1-8 further includes a number of ridges 60 (FIGS. 6-8) running generally between front side 20 and rear side 22 on the bottom of cushion 16 thus generally connecting the facial contact area to the front portion 28 and the headgear (not shown) coupled thereto. The localized increase in material thickness provides additional stability against patient interface device 10 rocking toward the nares of the patient.

FIG. 15A is a top cross-sectional view and FIG. 15B is a side view of a further embodiment of a patient interface device 600 according to the principles of the present invention. In this embodiment, patient interface device 600 includes a cushion 610 and stabilizing members 612 provided on each side of the cushion. In addition, the patient interface device includes a maxilla support assembly 630 that serves to transfer strapping forces to the maxilla supports, as indicated by arrows A. Maxilla support assembly 630 also helps to maintain the curvature of the cushion, i.e., prevent the cushion from collapsing as the cushion is forced against the face of the user.

Maxilla support assembly 630 includes a first portion 632 operatively coupled to a proximal end of cushion 610 and/or an elbow coupling 602 and a second portion 634 operatively coupled to stabilizing members 612. A support member 636 spans between first portion 632 and second portion 634. In this embodiment, the maxilla support assembly is intended to be as minimal as possible, and extends from the elbow coupling into a pocket (not shown) within the stabilizing member. The use of maxilla support assembly is particularly helpful in situations where the cushion is formed from a relatively low durometer.

The present invention contemplates that any portion of the maxilla support assembly 630 can be provided within the cavity defined by the cushion, provided in the wall of the cushion itself, provided external to the cushion, or any combination thereof. The maxilla support assembly is formed from a sufficiently rigid or semi-rigid material so as to transfer the forces to the stabilizing members. In an exemplary embodiment, at least a portion of the maxilla support assembly is flexible so as to allow flexing of the cushion as the strapping force is changed.

The maxilla support assembly can be formed from a variety of materials and can be either permanently or selectively attachable to the cushion and/or elbow coupling. In addition, the various components of the maxilla support assembly can have any one of a variety of sizes, shapes and geometries. FIGS. 16A and 16B illustrate examples of other such configurations for maxilla support assembly 630a and 630b.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A patient interface device comprising:
   a cushion defining a cavity therein, the cushion having a first side and an opposite second side with the cavity defined between the first side and the second side;
   a headgear coupled to the cushion adjacent the first side of the cushion, the headgear comprising at least one strap for use in securing the cushion to the head of a patient,
   wherein the cushion comprises:
      an aperture formed in the second side of the cushion providing access to the cavity, the aperture having a periphery adapted to sealingly engage about the nostrils of the patient when the cushion is disposed on the face of the patient; and
   a pair of stabilizing members directly coupled to, and extending upward from, the second side of the cushion, each stabilizing member being adapted to contact the face of the patient in a region adjacent to, but spaced from, the nose of the patient and below the orbital bone ridge of the patient in such a manner that strapping forces resulting from tightening of the at least one strap of the headgear, which would otherwise be directed near the nares of the patient, are instead concentrated onto outer portions of the patient's maxilla away from the nares, nose, and upper lip of the patient, and wherein each of the stabilizing members is integrally formed with the cushion; and
   a generally rigid elongated front portion coupled to the first side of the cushion, wherein the headgear is coupled to the cushion via the elongated front portion.

2. The patient interface device of claim 1, wherein the stabilizing members are disposed on opposite sides of the aperture.

3. The patient interface device of claim 1, wherein each of the stabilizing members are bounded by a grooved portion which is structured to allow each stabilizing member to articulate with respect to the cushion.

4. The patient interface device of claim 3, wherein the grooved portion comprises a baffle.

5. The patient interface device of claim 3, wherein the grooved portion comprises a locally thinned wall section.

6. The patient interface device of claim 1, wherein the stabilizing members are formed separately from, and selectively coupled to, the cushion.

7. The patient interface device of claim 1, wherein each stabilizing member comprises a cavity formed therein, and wherein the cavity of each stabilizing member is filled with one or more of a low durometer gel or foam.

8. The patient interface device of claim 1, wherein the cushion comprises a cradle shaped elongate hollow body and wherein the first side is of a generally convex shape and wherein the opposite second side is of a generally concave shape.

9. The patient interface device of claim 8, further comprising a generally rigid elongated front portion coupled to the first side of the cushion, the front portion having a first end, an opposite second end and an aperture disposed therebetween, wherein the aperture is adapted to be coupled to a patient circuit, and wherein each of the first end and opposite second end are adapted to be selectively coupled to a headgear for use in securing the patient interface device to the head of a patient.

10. The patient interface device of claim 9, wherein the front portion is coupled to the first side of the cushion via a hollow articulating portion.

11. The patient interface device of claim 10, wherein the hollow articulating portion includes an inward curved U-shaped portion disposed along an upper portion thereof.

12. The patient interface device of claim 1, further comprising a maxilla support assembly operatively coupled to the stabilizing members.

13. The patient interface device of claim 1, wherein the elongated front portion is coupled to the first side of the cushion via a hollow articulating portion.

14. A patient interface device comprising:
a cushion defining a cavity therein, the cushion having a first side and an opposite second side; and
a headgear coupled to the cushion, the headgear comprising at least one strap for use in securing the cushion to the head of a patient,
wherein the cushion comprises:
an aperture formed in the second side providing access to the cavity, the aperture having a periphery adapted to sealingly engage about the nostrils of the patient when the cushion is disposed on the face of the patient; and
a pair of stabilizing members coupled to, and extending upward from, the cushion, each stabilizing member being adapted to contact the face of the patient in a region adjacent to, but spaced from, the nose of the patient and below the orbital bone ridge of the patient in such a manner that strapping forces resulting from tightening of the at least one strap of the headgear, which would otherwise be directed near the nares of the patient, are instead concentrated onto outer portions of the patient's maxilla away from the nares, nose, and upper lip of the patient,
wherein each stabilizing member comprises a cavity formed therein, and
wherein each cavity is in communication with the cavity of the cushion and wherein each cavity is adapted to be inflated by one or both of an applied system pressure and an exhalation pressure of the patient.

15. A cushion for use in a patient interface device, the cushion comprising:
a front side structured to be coupled to a headgear for securing the cushion to a patient;
an aperture formed in a patient facing side opposite the front side, the aperture providing access to a cavity defined within the cushion between the front side and the patient facing side, the aperture having a periphery adapted to sealingly engage about the nostrils of a patient when the cushion is disposed on the face of a patient; and
a pair of stabilizing members coupled to, and extending rearward and upward from, the patient facing side of the cushion, each stabilizing member being adapted to contact the face of the patient in a region adjacent to, but spaced from, the nose and below the orbital bone ridge of the patient in such a manner that strapping forces, which would otherwise be directed near the nares of the patient, are instead concentrated onto the patient's maxilla away from the nares, nose and upper lip of the patient,
wherein each of the stabilizing members is integrally formed with the cushion, wherein each stabilizing member comprises a cavity formed therein, wherein each cavity is in communication with the cavity of the cushion, and wherein each cavity is adapted to be inflated to one or both of an applied system pressure and an exhalation pressure of the patient.

16. The cushion of claim 15, wherein the stabilizing members are disposed on opposite sides of the aperture.

17. The cushion of claim 16, wherein each of the stabilizing members are bounded by a grooved portion which is structured to allow each stabilizing member to articulate with respect to the cushion.

18. The cushion of claim 17, wherein the grooved portion comprises a baffle.

19. The cushion of claim 15, further comprising a generally rigid elongated front portion coupled to the first side of the cushion, wherein the elongated front portion is structured to be coupled to the headgear for securing the cushion to a patient.

20. The cushion of claim 19, wherein the elongated front portion is coupled to the first side of the cushion via a hollow articulating portion.

* * * * *